US011304937B2

(12) United States Patent
Funaki et al.

(10) Patent No.: US 11,304,937 B2
(45) Date of Patent: Apr. 19, 2022

(54) MEDICINAL COMPOSITION FOR INHALATION

(71) Applicant: Shionogi & Co., Ltd., Osaka (JP)

(72) Inventors: Takeshi Funaki, Hyogo (JP); Yukiko Nishino, Hyogo (JP); Yuki Masuda, Hyogo (JP); Koichi Tsubone, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 54 days.

(21) Appl. No.: 16/316,261

(22) PCT Filed: Jul. 12, 2017

(86) PCT No.: PCT/JP2017/025337
§ 371 (c)(1),
(2) Date: Jan. 8, 2019

(87) PCT Pub. No.: WO2018/012516
PCT Pub. Date: Jan. 18, 2018

(65) Prior Publication Data
US 2019/0231764 A1  Aug. 1, 2019

(30) Foreign Application Priority Data

Jul. 12, 2016  (JP) .............................. JP2016-137661

(51) Int. Cl.
| | | |
|---|---|---|
| *A61K 31/4418* | (2006.01) | |
| *A61K 47/44* | (2017.01) | |
| *A61K 47/38* | (2006.01) | |
| *A61K 47/12* | (2006.01) | |
| *A61K 47/24* | (2006.01) | |
| *A61K 47/10* | (2017.01) | |
| *A61P 11/00* | (2006.01) | |
| *A61K 47/26* | (2006.01) | |
| *A61K 47/14* | (2017.01) | |
| *A61K 9/48* | (2006.01) | |
| *A61K 47/32* | (2006.01) | |
| *A61K 9/00* | (2006.01) | |
| *A61K 9/14* | (2006.01) | |

(52) U.S. Cl.
CPC ........ *A61K 31/4418* (2013.01); *A61K 9/0075* (2013.01); *A61K 9/143* (2013.01); *A61K 9/145* (2013.01); *A61K 9/146* (2013.01); *A61K 9/48* (2013.01); *A61K 47/10* (2013.01); *A61K 47/12* (2013.01); *A61K 47/14* (2013.01); *A61K 47/24* (2013.01); *A61K 47/26* (2013.01); *A61K 47/32* (2013.01); *A61K 47/38* (2013.01); *A61K 47/44* (2013.01); *A61P 11/00* (2018.01)

(58) Field of Classification Search
None
See application file for complete search history.

(56) References Cited

U.S. PATENT DOCUMENTS

| | | | |
|---|---|---|---|
| 6,645,466 B1 | 11/2003 | Keller et al. | |
| 2004/0109827 A1 | 6/2004 | Onoue et al. | |
| 2004/0202616 A1 | 10/2004 | Keller et al. | |
| 2009/0191265 A1* | 7/2009 | Radhakrishnan | ......... A61P 9/10 424/452 |
| 2010/0040691 A1 | 2/2010 | Richards et al. | |
| 2013/0310424 A1* | 11/2013 | Surber | ................ A61K 9/0078 514/345 |
| 2014/0341998 A1 | 11/2014 | Onoue et al. | |
| 2016/0045435 A1 | 2/2016 | Green | |

FOREIGN PATENT DOCUMENTS

| | | |
|---|---|---|
| EP | 1 036 562 | 9/2000 |
| EP | 1 356 816 | 10/2003 |
| EP | 2 756 840 | 7/2014 |
| JP | 2-215719 | 8/1990 |
| JP | 2002-284703 | 10/2002 |
| JP | 2003-34652 | 2/2003 |
| JP | 2010-132605 | 6/2010 |
| JP | 2011-19970 | 2/2011 |
| JP | 2011-93849 | 5/2011 |
| JP | 2011-231124 | 11/2011 |
| JP | 2014-227371 | 12/2014 |
| WO | 90/09176 | 8/1990 |
| WO | 94/26249 | 11/1994 |
| WO | 01/13885 | 3/2001 |
| WO | 2005/046636 | 5/2005 |
| WO | 2007/038315 | 4/2007 |
| WO | 2007/064738 | 6/2007 |
| WO | 2008/000482 | 1/2008 |
| WO | 2010/048716 | 5/2010 |
| WO | 2011-120779 | 10/2011 |
| WO | 2012/106382 | 8/2012 |

(Continued)

OTHER PUBLICATIONS

Seto et al., "pment of an Improved Inhalable Powder Formulation of Pirfenidone by Spray-Drying: In Vitro Characterization and Pharmacokinetic Profiling", Pharm Res, 33, 2016, pp. 1447-1455. (Year: 2016).*
International Search Report dated Aug. 15, 2017 in International Application No. PCT/JP2017/025337.
Pharmacia (1997) vol. 33, No. 4, 370-375.
Pharmacia (1997) vol. 33, No. 4, 376-381.
M.P. Timsina et al., "Drug delivery to the respiratory tract using dry powder inhalers", Int. Journal of Pharmaceutics (1994) 101, 1-13.
Satomi Onoue et al., "Inhalable Powder Formulation of Pirfenidone with Reduced Phototoxic Risk for Treatment of Pulmonary Fibrosis", Pharmaceutical Research (2013), 30(6), 1586-1596.
Satomi Onoue et al., "In vitro and in vivo characterization on amorphous solid dispersion of cyclosporine A for inhalation therapy", Journal of Controlled Release (2009), 138(1), 16-23.

(Continued)

*Primary Examiner* — Melissa L Fisher
(74) *Attorney, Agent, or Firm* — Wenderoth, Lind & Ponack, L.L.P.

(57) ABSTRACT

The present invention provides a particle comprising pirfenidone and a lipid, particularly magnesium stearate, and having a mean particle diameter of 5 μm or less, and a powder formulation comprising the particle and a carrier.

13 Claims, 2 Drawing Sheets

(56) References Cited

FOREIGN PATENT DOCUMENTS

| WO | 2013/039167 | 3/2013 |
| WO | 2014/155134 | 10/2014 |

OTHER PUBLICATIONS

Yohei Kawabata et al., "Stable dry powder inhaler formulation of tranilast attenuated antigen-evoked airway inflammation in rats", European Journal of Pharmaceutic and Biopharmaceutics (2011), 77(1), 178-181.

Yoshiaki Kawashima et al., "Effect of surface morphology of carrier lactose on dry powder inhalation property of pranlukast hydrate", Int. Journal of Pharmaceutics (1998)172, 179-188.

The 30th Annual Meeting of The Academy of Pharmaceutical Science and Technology, Japan, Abstracts p. 118.

International Preliminary report on Patentability dated Jan. 24, 2019 in International (PCT) Application No. PCT/JP2017/025337.

Satomi Onoue et al., "Development of Inhalable Nanocrystalline Solid Dispersion of Tranilast for Airway Inflammatory Diseases", Journal of Pharmaceutical Sciences, vol. 100, No. 2, pp. 622-633, Feb. 2011.

Extended European Search Report, dated Feb. 7, 2020 in corresponding European Patent Application No. 17827643.2.

Philippe Begat et al., "The Influence of Force Control Agents on the Cohesive-Adhesive Balance in Dry Powder Inhaler Formulations", KONA, 2005, No. 23, pp. 109-121.

* cited by examiner

Figure 1

Inventive particles 1

Comparative particles 1

MEDICINAL COMPOSITION FOR INHALATION

TECHNICAL FIELD

The present invention relates to a particle comprising pirfenidone as a medicinal ingredient. The present invention further relates to a powder respirable formulation comprising a particle comprising pirfenidone and a lipid, particularly magnesium stearate, and a carrier.

BACKGROUND ART

Inhalation therapy has been applied for treatment of lung and respiratory tract diseases, diagnosis of diseases, transrespiratory tract and transpulmonary whole body medication, prophylaxis of diseases, transrespiratory tract immunity desensitization therapy, etc. as a medicinal use for transrespiratory organs. However, the adaptation-determining method of this therapy is fully examined for neither of the cases. Therefore, development of the corresponding respiratory formulation is desired.

As features of a general respiratory formulation, recognized are 1) quick expression of medicinal effects, 2) gradual reduction of side effects, 3) possibility of small dose administration, 4) avoidance of the first-pass effect, etc. When target regions are lungs, the respiratory formulation is equipped with further outstanding features by having a large surface area equal to small intestine.

In applying the respiratory formulation as a targeting therapy, it is necessary to consider a selection-criteria method of the respiratory formulation from the viewpoints of not only efficacy to disease but also a generation method of medicine particles, target delivery sites, and relevancy of the basic physical properties of medicine to them. Now, the respiratory formulation is used for bronchodilators, mucosa solubilizers, antibiotics, antiallergic agents, steroids, vaccines, etc., and in the case of their clinical application, the site of action of an inhalant, the mechanism of the action, the composition, direction for use, etc., are considered to be important factors.

Recent years, in treatment of bronchial asthma or chronic lung disease, a dry powder inhaler (DPI) has come to attract attention. This form has an advantage that, in addition to the features of the above-mentioned respiratory formulation, a medicine can be stored in a stable form for a long period of time. In DPI, there is a close relationship between a particle diameter of medicine particles being inhaled by a patient and deposition to the respiratory tract, and the aerodynamics correlation is recognized between the size of medicine particle diameter and the deposition of the medicine in the trachea and lungs (Non-patent Document 1). Specifically, it is generally known that the optimal sizes of medicine particles which can be delivered to the bronchi or the lungs are particles which have an aerodynamics diameter of about 1 to 6 μm (Non-patent Document 2).

Preferably, particles of several μm or less reach alveoli, and since they are efficiently absorbed from lung mucosa and migrate into blood, the particle size is important. However, the more the particles get fine, the more the fluidity of powder gets worse and, as a result, decreases in filling precision and handling property at the time of production are concerned. Then, in order to solve these problems in handling of a DPI formulation, a method is well known, which mixes particles described later with a carrier. According to this method, by making particles adhere to the carrier surface via intermolecular interaction, the cohesive force of particles is weakened, and the particle diameter is increased further as a whole, and thus, the fluidity of the formulation is improved. Examples of other methods include granulation of a medicine, a surface treatment method, and a spray drying method (Patent Documents 1 to 4). Moreover, the use of magnesium stearate for preparation of a DPI formulation is also known (Patent Documents 5 and 6).

Here, pirfenidone is the world's first anti-fibrosis agent approved as an agent to be applied for idiopathic pulmonary fibrosis. The action mechanism is production modulation for various cytokines, such as inflammatory cytokine and anti-inflammation cytokine, and for growth factors which participate in fibrosis formation, and the anti-fibrosis effect is exerted based on complex effects, such as fibroblast multiplication depressant action and collagen production depressant action. In comparison between pirfenidone and prednisolone, while prednisolone exhibited only an anti-inflammatory effect, pirfenidone exhibited both anti-inflammatory effect and anti-fibrosis effect. Consequently, pirfenidone is expected to provide more effective therapeutic results than steroid. Although it has been sold since 2008 in Japan, and is widely used for pulmonary fibrosis, patients who have taken pirfenidone could have showed drug-induced photodermatosis as a side effect, and their expression frequency results in about 50 percent. In order to avoid this problem, a suitable dosage form which can easily exhibit its effect on lung local parts has been desired. However, only oral pirfenidone formulation has been marketed till the present. That is, development is desired strongly for new dosage forms which will reduce a photodermatosis risk, a side effect of pirfenidone, and will bring about safer pulmonary fibrosis treatment. Furthermore, respiratory formulations are micronized particles and thus can have properties undesirable as respiratory formulations when particles are condensed to increase the particle diameters under humidification conditions. Moreover, a respiratory formulation containing pirfenidone at a high concentration is desired for pirfenidone to exhibit a sufficient medicinal effect.

Respiratory formulations comprising pirfenidone, which have been reported, are, a powder formulation comprising micronized particles comprising pirfenidone and lactose, and a carrier (Patent Document 7, Non-patent Document 3), a solid dispersion comprising pirfenidone and a controlled-release base (Patent Document 8), and an aqueous solution for inhalation administration comprising pirfenidone and a cosolvent (Patent Document 9).

DPI formulations comprising micronized particles adsorbed onto the carrier surface, which have been reported, are a cyclosporin formulation (Non-patent Document 4), a tranilast formulation (Patent Document 10, Non-patent Documents 5 and 6), a formulation of a glycopyrronium salt (Patent Document 11), and a formulation comprising micronized particles as a spray-dried product (SD product) (Non-patent Document 8), for example.

However, none of these documents describe a powder respirable formulation having a mean particle diameter that does not increase under high temperatures or humidification and containing a medicine at a high concentration as in the case of the present invention.

PRIOR ART DOCUMENTS

Patent Documents

[Patent Document 1] WO99/27911
[Patent Document 2] JP2011-19970
[Patent Document 3] JP2003-526629

[Patent Document 4] JP2003-34652
[Patent Document 5] JP2011-231124
[Patent Document 6] JP2007-511502
[Patent Document 7] WO2013/039167
[Patent Document 8] JP2014-227371
[Patent Document 9] JP2014-503598
[Patent Document 10] JP2011-93849
[Patent Document 11] JP2009-541393

Non-Patent Documents

[Non-patent Document 1] Pharmacia (1997) Vol. 33, No. 6, 98-102
[Non-patent Document 2] Int. J. Pharm. (1994) 101, 1-13
[Non-patent Document 3] Pharmaceutical Research (2013), 30(6), 1586-1596
[Non-patent Document 4] Journal of Controlled Release (2009), 138(1), 16-23
[Non-patent Document 5] Journal of Pharmaceutical Sciences (2011), 100(2), 622-633
[Non-patent Document 6] European Journal of Pharmaceutic and Biopharmaceutics (2011), 77(1), 178-181
[Non-patent Document 7] Int. J. Pharm. (1998) 172, 179-188
[Non-patent Document 8] The 30th Annual Meeting of The Academy of Pharmaceutical Science and Technology, Japan, Abstracts p. 118

SUMMARY OF INVENTION

Problems to be Solved by the Invention

The present invention provides a respiratory formulation comprising pirfenidone, which has a stable mean particle diameter that does not increase even under high temperatures or humidity, and comprises pirfenidone at a high concentration. The present invention further preferably provides a respiratory formulation of pirfenidone having excellent inhalation properties, which can control the whole body exposure of a medicine having a side effect of drug-induced photodermatosis, especially transmigration of the medicine to the skin.

Means for Solving the Problems

As a result of intensive studies to solve the above-mentioned problems, inventors of the present invention have succeeded in obtaining a powder formulation having excellent fluidity, filling property, dispersibility and inhalation properties, by: grinding, particularly performing jet mill grinding of pirfenidone in the coexistence with a lipid, particularly magnesium stearate, so as to produce particles having a particle diameter that enables aerodynamic delivery to lungs; mixing well the obtained particles with a carrier having a particle diameter with a good conformity with the particles; and then causing the resultant to be efficiently delivered to the respiratory tissue (e.g., upper respiratory tract, lungs) of a recipient. Then, the inventors of the present invention have completed the present invention. That is, the present invention provides the following (1) to (21) and (1A) to (20A).
(1) A micronized particle comprising pirfenidone and a lipid and having a mean particle diameter of 5 μm or less.
(2) The micronized particle according to the above (1), wherein the lipid is one or more lipids selected from the group consisting of stearic acid, magnesium stearate, calcium stearate, sucrose fatty acid ester, sodium stearyl fumarate, stearyl alcohol, cetyl alcohol, hydrogenated oil, glyceryl behenate, and lecithin.
(3) The micronized particle according to the above (2), wherein the lipid is magnesium stearate.
(4) The micronized particle according to any one of the above (1) to (3), wherein the ratio between pirfenidone and the lipid is in the range of 10:1 to 500:1 in weight ratio.
(5) A powder formulation comprising the micronized particle according to any one of the above (1) to (4) and a carrier.
(6) The powder formulation according to the above (5), wherein the carrier is selected from the group consisting of a saccharide, a sugar alcohol and a macromolecular polymer.
(7) The powder formulation according to the above (5), wherein the carrier is a saccharide and the saccharide is selected from the group consisting of lactose, glucose, saccharose, trehalose and sucrose.
(8) The powder formulation according to the above (7), wherein the carrier is a saccharide and the saccharide is lactose.
(9) The powder formulation according to the above (5), wherein the carrier is a sugar alcohol, and the sugar alcohol is selected from the group consisting of erythritol, mannitol and sorbitol.
(10) The powder formulation according to the above (5), wherein the carrier is a macromolecular polymer, and the macromolecular polymer is selected from the group consisting of calcium carmellose, polyvinyl pyrrolidone and methylcellulose.
(11) The powder formulation according to any one of the above (5) to (10), wherein the carrier has a mean particle diameter of 10 μm to 250 μm.
(12) The powder formulation according to any one of the above (5) to (11), wherein the ratio between the micronized particle and the carrier is 0.1:100 to 100:0.1 in weight ratio.
(13) The micronized particle or the powder formulation according to any one of the above (1) to (12), which is used for transpulmonary inhalation.
(14) A powder formulation for transpulmonary inhalation, comprising pirfenidone, magnesium stearate, and lactose.
(15) The powder formulation according to any one of the above (5) to (14), wherein the content of pirfenidone is 5 wt % to 30 wt %.
(16) The powder formulation according to any one of the above (5) to (15), wherein the content of magnesium stearate is 0.02 wt % to 0.5 wt %.
(17) The powder formulation according to the above (15) or (16), wherein the content of pirfenidone is 5 wt % to 30 wt %, the content of magnesium stearate is 0.02 wt % to 0.5 wt %, and the content of lactose is 69.5 wt % to 94.98 wt %.
(18) A capsule, encapsulating the micronized particle or the powder formulation according to any one of the above (1) to (17).
(19) A grinding adjuvant of pirfenidone, comprising magnesium stearate.
(20) A process for producing the micronized particle or the powder formulation according to any one of the above (1) to (18), wherein pirfenidone and a lipid are mixed, and then the mixture is micronized using a jet mill to produce the micronized particle or the powder formulation.
(21) A process for producing the powder formulation according to any one of the above (5) to (18), wherein a micronized particle comprising pirfenidone and a lipid and having a mean particle diameter of 5 μm or less is mixed with a carrier to produce the powder formulation.
(1A) A micronized particle comprising pirfenidone and a lipid and having a mean particle diameter of 5 μm or less.

(2A) The micronized particle according to the above (1A), wherein the lipid is one or more lipids selected from the group consisting of stearic acid, magnesium stearate, calcium stearate, sucrose fatty acid ester, sodium stearyl fumarate, stearyl alcohol, cetyl alcohol, hydrogenated oil, glyceryl behenate and lecithin.

(3A) The micronized particle according to the above (2A), wherein the lipid is magnesium stearate.

(4A) The micronized particle according to any one of the above (1A) to (3A), wherein the ratio between pirfenidone and the lipid is in the range of 10:1 to 500:1 in weight ratio.

(5A) A powder formulation comprising the micronized particle according to any one of the above (1A) to (4A) and a carrier.

(6A) The powder formulation according to the above (5A), wherein the carrier is selected from the group consisting of a saccharide, a sugar alcohol and a macromolecular polymer.

(7A) The powder formulation according to the above (5A), wherein the carrier is a saccharide, and the saccharide is selected from the group consisting of lactose, glucose, saccharose, trehalose and sucrose.

(8A) The powder formulation according to the above (7A), wherein the carrier is a saccharide, and the saccharide is lactose.

(9A) The powder formulation according to the above (5A), wherein the carrier is a sugar alcohol, and the sugar alcohol is selected from the group consisting of erythritol, mannitol and sorbitol.

(10A) The powder formulation according to the above (5A), wherein the carrier is a macromolecular polymer, and the macromolecular polymer is selected from the group consisting of calcium carmellose, polyvinyl pyrrolidone and methylcellulose.

(11A) The powder formulation according to any one of the above (5A) to (10A), wherein the carrier has a mean particle diameter of 10 μm to 250 μm.

(12A) The powder formulation according to any one of the above (5A) to (11A), wherein the ratio between the micronized particle and the carrier is 0.1:100 to 100:0.1 in weight ratio.

(13A) The micronized particle or the powder formulation according to any one of the above (1A) to (12A), which is used for transpulmonary inhalation.

(14A) A powder formulation for transpulmonary inhalation, comprising pirfenidone, magnesium stearate and lactose.

(15A) The powder formulation according to any one of the above (5A) to (14A), wherein the content of pirfenidone is 5 wt % to 30 wt %.

(16A) The powder formulation according to the above (15A), wherein the content of pirfenidone is 5 wt % to 30 wt %, the content of magnesium stearate is 0.01 wt % to 0.5 wt %, and the content of lactose is 69.5 wt % to 94.99 wt %.

(17A) A capsule encapsulating the micronized particle or the powder formulation according to any one of the above (1A) to (16A).

(18A) A grinding adjuvant of pirfenidone, comprising magnesium stearate.

(19A) A process for producing the micronized particle according to any one of the above (1A) to (17A), wherein pirfenidone and a lipid are mixed and then the mixture is micronized using a jet mill to produce the micronized particle.

(20A) A process for producing the powder formulation according to any one of the above (5A) to (17A), wherein a micronized particle comprising pirfenidone and a lipid and having a mean particle diameter of 5 μm or less is mixed with a carrier.

Effects of the Invention

The present invention enables inhalation therapy using pirfenidone powder. As a result of measuring the mean particle diameter of pirfenidone micronized particles of the present invention under high temperatures or humidification, the mean particle diameter remained almost unchanged for prolonged periods. Moreover, as a result of assessing the powder formulation of the present invention using a cascade impactor which is an artificial respiratory tract and a lung model, it was revealed that FPF values indicating the arrival of the medicine at lungs or the delivery dose at stages 2 to 7 were high. The data demonstrate that the powder formulation of the present invention has high temporal stability, delivers the medicine very specifically to lungs, makes it possible to treat inflammatory lung disease, pulmonary fibrosis, etc., with an extremely low dose thereof compared with an oral administration, and can reduce the photodermatosis risk which is a main side effect of pirfenidone by preventing the skin transmigration of the medicine.

EMBODIMENTS TO CARRY OUT THE INVENTION

Hereinafter, the present invention is described in detail.

[1] Process for Producing Micronized Particle Comprising Pirfenidone and Lipid

An example of the process for producing a micronized particle of the present invention (hereinafter, may also be referred to as the "inventive particle") comprising pirfenidone and a lipid, particularly magnesium stearate, and having a mean particle diameter of 5 μm or less is a process, which comprises mixing pirfenidone and a lipid, particularly magnesium stearate, and then grinding the thus mixed particles. Examples of a general grinding process include a dry grinding process and a wet grinding process. As known general dry grinding processes, specifically ball milling, high velocity revolution trituration and impact milling, and jet milling, etc., are known. As known ball mills, a rolling ball mill, a centrifugal ball mill, a vibration ball mill, and a planetary ball mill are known, and these can perform grinding based on principles, such as grinding, rotation, vibration, and impact. There are a disc mill and a roller mill as a high velocity revolution trituration mill, and as a high velocity revolution impact mill, there are devices such as a cutter mill (knife mill), a hammer mill (atomizer), a pin mill, a screen mill, etc., which perform grinding by rotation impact in addition to shearing. Many jet mills mainly perform grinding with impact and examples of the types thereof include a particle-particle collision type, a particle-collision plate collision type, and a nozzle sucking type (blow off).

Jet mill grinding involves applying an impact and compression using a jet mill grinder to grind powder. Specifically, several atmospheres of compressed air, superheated steam or the like is ejected from a nozzle of a jet mill grinder, ground raw materials are caught in the jet, and then ultrafine grinding is performed by collision between powders or between powders and material walls. Specifically, the mixed powder of pirfenidone and a lipid, particularly magnesium stearate is introduced from a feed hopper, the mixed powder of pirfenidone and the lipid, particularly magnesium stearate introduced into the mill at a ultrasonic speed accelerated by the ventury nozzle was subjected to mutual collision and mutual frictional grinding within a grinding zone formed of a fluid discharged from a grinding nozzle installed at a lower part of the mill, and then discharged in fines of several microns. When the inventive particles are produced by a jet mill grinding process, as a jet mill grinder, specifically Alpine spiral jet mill (HOSOKAWA MICRON) is used. Supply air pressure is 0.1 MPa to 1 MPa, preferably 0.2 MPa to 0.8 MPa, more preferably 0.3 MPa to 0.7 MPa, and particularly preferably 0.6 MPa. Grinding air pressure is 0.05 MPa to 1 MPa, preferably 0.15 MPa to 0.8 MPa, more preferably 0.25 MPa to 0.7 MPa, and particularly preferably 0.6 MPa.

Hammer mill grinding involves grinding powder by applying an impact using a hammer mill grinder. The hammer mill grinder is a grinder having a mechanism by which an impact is applied to and grinding raw materials to be ground using a high speed rotary hammer.

Ball mill grinding involves grinding powder using a ball mill grinder. The ball mill grinder has a mechanism by which a main mill body that is a cylindrical rotary container rotates to lift the ball and raw materials to be ground with the resulting frictional force and centrifugal force, and then causes them to fall due to gravity, during which grinding proceeds due to the impact and friction applied by the ball.

Examples of the lipid include a simple lipid, a complex lipid, and a derived lipid. The term "simple lipid" refers to an ester of alcohol and fatty acid. As alcohol portions, glycerin, sterol and the like in addition to straight-chain alcohol are used. As fatty acid, various saturated fatty acids or unsaturated fatty acids are used. The term "complex lipid" refers to a lipid containing phosphoric acid and sugar in the molecule, in which generally sphingosine or glycerin serves as the skeleton. The term "derived lipid" refers to a compound that is induced from a simple lipid or a complex lipid via hydrolysis. However, lipids that do not fall into these categories also exist.

Specific examples of lipids include stearic acid, magnesium stearate, calcium stearate, sucrose fatty acid ester, sodium stearyl fumarate, stearyl alcohol, cetyl alcohol, hydrogenated oil, glyceryl behenate and lecithin, and preferably stearic acid, magnesium stearate, and calcium stearate, and is more preferably magnesium stearate.

The inventor of the present invention has discovered that particles having particle diameters, by which the particles can be aerodynamically delivered to the lungs, can be produced by performing jet mill grinding of pirfenidone in the coexistence of pirfenidone with a lipid, particularly magnesium stearate under specific conditions.

In the inventive particles, the weight ratio between pirfenidone and a lipid, particularly magnesium stearate, is in the range of 1:1 to 1000:1. If pirfenidone exists in an amount higher than this range, particle diameters by which the particles can be aerodynamically delivered to the lungs may not be obtained. If magnesium stearate exists in an amount higher than this range, pirfenidone may lose its pharmacological activity. In the inventive particles, the weight ratio between pirfenidone and magnesium stearate is preferably 2:1 to 750:1, more preferably 10:1 to 500:1, further preferably, 15:1 to 100:1, and particularly preferably 33.33:1.

According to another embodiment, in the inventive particles, the weight ratio between pirfenidone and magnesium stearate is in the range of 3.75:1 to 302.03:1. According to yet another embodiment, in the inventive particles, examples of the weight ratio between pirfenidone and magnesium stearate include 33.36:1, 59.98:1, 302.03:1, 33.33:1, 16.67:1, 7.5:1, 6.25:1, and 3.75:1, and another example of the same is particularly preferably 33.33:1.

The mean particle diameter of a lipid, and particularly magnesium stearate can be lowered to about 2 μm by jet mill grinding. Moreover, regarding the grade of magnesium stearate, commercially available light magnesium stearate, or, magnesium stearate for inhalation can be used.

In the inventive particles, the particle diameter is important for pirfenidone to reach the lungs. The particle diameter is measured by particle size analysis laser diffraction methods. The particle size analysis laser diffraction methods involve irradiating a group of particles with a laser beam, and then finding the particle size distribution from the intensity distribution pattern of the thus emitted diffraction/scattered light via calculation. Particle diameters in the cumulative particle size distribution curves in terms of volume, 10%, 50%, and 90% obtained by the particle size analysis laser diffraction methods are designated as 10% particle diameter (D10), mean particle diameter (50% particle diameter (D50), and 90% particle diameter (D90), respectively.

As a result of mixing of pirfenidone, and a lipid, particularly magnesium stearate in the inventive particles, the inventive particles had a mean particle diameter of 5 μm or less as measured by the particle size analysis laser diffraction methods. This mean particle diameter makes it possible for the inventive particles to separate from the carrier after administration, and then to be delivered to target sites such as the bronchi, the lungs, or the like. The inventive particles have a mean particle diameter of preferably 0.5 μm to 5 μm. The 10% particle diameter (D10) is 0.1 μm to 3 μm, and preferably 0.5 μm to 2.5 μm. The 90% particle diameter (D90) is 5 μm to 15 μm, and preferably 6 μm to 13 μm.

[2] Carrier

According to another embodiment of the present invention, a carrier is used for preventing the agglomeration of pirfenidone before the administration of the powder formulation, and for increasing the dispersibility of the inventive particles as an inhalation formulation upon administration through the formation of a complex (described later) with the inventive particles. Especially, when an inhalation operation using an inhaler is carried out for application to the bronchi or the lungs, the inventive particles are efficiently separated from the carrier after inhalation and, as a result, the dispersibility of pirfenidone is improved. When the carrier is used for designing a DPI formula, it is desirable to definitely release the medicine from a capsule, a blister pack, or a device, and to separate the medicine from the carrier surface with high probability. It is necessary to design the formulation in considering enough these points. When a carrier is used, fluidity of a formulation, prevention of agglomeration of a medicine, and the propriety of dose increase and decrease, etc., are important. From these viewpoints, a carrier in the present invention is preferably powdered. As selection criteria of a carrier, easiness and workability for handling are required, not to mention toxicity or physicochemical stability. Specific examples of a carrier that can be used in the present invention include, but are not limited to, saccharides such as lactose, glucose, fructose, sucrose, malt sugar, saccharose, trehalose and dextrans, sugar alcohols such as erythritol, sorbitol, and mannitol, macromolecular polymers such as microcrystalline cellulose, methylcellulose, hydroxypropylcellulose, hydroxypropylmethylcellulose, carmellose sodium, pullulan, dextrin, gum arabic, agar, gelatin, tragacanth, sodium alginate, polyvinyl pyrrolidone, and polyvinyl alcohol, and general excipients such as calcium sulfate, calcium carbonate, talc, and titanium oxide. Preferable carriers are saccharides or sugar alcohols, and a more preferable carrier is lactose or erythritol. Among these examples, lactose having stability that has been established, being neutral, having low reactivity, and having slight sweetness is useful in many respects, and thus the usefulness of lactose as a carrier for DPI has been confirmed (Non-patent Document 7).

When the pharmaceutical composition of the present invention is in a form to be administered using an inhaler, a carrier to be used in this case has an aerodynamically acceptable particle size distribution. Specifically, a carrier to be used herein satisfies any one of the following conditions.

(Condition-1):
The particle size distribution as measured by the particle size analysis laser diffraction methods is as follows:
10% particle diameter of lactose: 2.67 μm,
50% particle diameter of lactose: 17.48 μm, and
90% particle diameter of lactose: 74.45 μm.

(Condition-2):
The particle size distribution as measured by the particle size analysis laser diffraction methods is as follows:
10% particle diameter of lactose: 19 μm-43 μm,
50% particle diameter of lactose: 53 μm-66 μm, and
90% particle diameter of lactose: 75 μm-106 μm.

(Condition-3):
The particle size distribution as measured by the particle size analysis laser diffraction methods is as follows:
10% particle diameter of lactose: 70 μm-105 μm,
50% particle diameter of lactose: 110 μm-155 μm, and
90% particle diameter of lactose: 160 μm-215 μm.

(Condition-4):
The particle size distribution as measured by the particle size analysis laser diffraction methods is as follows:
10% particle diameter of lactose: 10 μm-25 μm,
50% particle diameter of lactose: 40 μm-70 μm, and
90% particle diameter of lactose: 80 μm-120 μm.

(Condition-5):
The particle size distribution as measured by the air entrainment methods is as follows:
Fraction of less than 45 μm: 90%-100%,
Fraction of less than 63 μm: 98%-100%, and
Fraction of less than 150 μm: 100%.

(Condition-6):
The particle size distribution as measured by the particle size analysis laser diffraction methods is as follows:
10% particle diameter of lactose: 35 μm-65 μm,
50% particle diameter of lactose: 95 μm-125 μm, and
90% particle diameter of lactose: 160 μm-190 μm.

(Condition-7):
The particle size distribution as measured by the particle size analysis laser diffraction methods is as follows:
10% particle diameter of lactose: 3 μm-7 μm,
50% particle diameter of lactose: 37 μm-61 μm, and
90% particle diameter of lactose: 124 μm-194 μm.

(Condition-8):
The particle size distribution as measured by the particle size analysis laser diffraction methods is as follows:
10% particle diameter of lactose: 100 μm-150 μm,
50% particle diameter of lactose: 180 μm-250 μm, and
90% particle diameter of lactose: 270 μm-340 μm.

(Condition 9):
The particle size distribution as measured by the particle size analysis laser diffraction methods is as follows:
10% particle diameter of lactose: 30 μm-60 μm,
50% particle diameter of lactose: 70 μm-110 μm, and
90% particle diameter of lactose: 110 μm-150 μm.

Particulate lactose of the above condition-1 to condition-9 are as specifically shown in lactose 1 to lactose 9, respectively in Table 1.

TABLE 1

|  | Lactose (Trade name) | Particle size distribution |
| --- | --- | --- |
| Lactose 1 | Pharmatose 200M (DFE Pharma) | 10% particle diameter of lactose: 2.67 μm<br>50% particle diameter of lactose: 17.48 μm<br>90% particle diameter of lactose: 74.45 μm<br>(Measurement: Particle size analysis laser diffraction methods) |
| Lactose 2 | Respitose SV003 (DFE Pharma) | 10% particle diameter of lactose: 19 μm-43 μm<br>50% particle diameter of lactose: 53 μm-66 μm<br>90% particle diameter of lactose: 75 μm-106 μm<br>(Measurement: Particle size analysis laser diffraction methods) |
| Lactose 3 | InhaLac 120 (Molkerei MEGGLE Wasserburg GmbH&Co. KG) | 10% particle diameter of lactose: 70 μm-105 μm<br>50% particle diameter of lactose: 110 μm-155 μm<br>90% particle diameter of lactose: 160 μm-215 μm<br>(Measurement: Particle size analysis laser diffraction methods) |
| Lactose 4 | InhaLac 250 (Molkerei MEGGLE Wasserburg GmbH&Co. KG) | 10% particle diameter of lactose: 10 μm-25 μm<br>50% particle diameter of lactose: 40 μm-70 μm<br>90% particle diameter of lactose: 80 μm-120 μm<br>(Measurement: Particle size analysis laser diffraction methods) |
| Lactose 5 | Respitose ML006 (DFE Pharma) | Fraction of less than 45 μm: 90-100%<br>Fraction of less than 63 μm: 98-100%<br>Fraction of less than 150 μm: 100%<br>(Measurement: Air entrainment methods) |
| Lactose 6 | Respitose SV010 (DFE Pharma) | 10% particle diameter of lactose: 35 μm-65 μm<br>50% particle diameter of lactose: 95 μm-125 μm<br>90% particle diameter of lactose: 160 μm-190 μm<br>(Measurement: Particle size analysis laser diffraction methods) |

TABLE 1-continued

| | Lactose (Trade name) | Particle size distribution |
|---|---|---|
| Lactose 7 | Respitose ML001 (DFE Pharma) | 10% particle diameter of lactose: 3 μm-7 μm<br>50% particle diameter of lactose: 37 μm-61 μm<br>90% particle diameter of lactose: 124 μm-194 μm<br>(Measurement: Particle size analysis laser diffraction methods) |
| Lactose 8 | InhaLac 70 (Molkerei MEGGLE Wasserburg GmbH&Co. KG) | 10% particle diameter of lactose: 100 μm-150 μm<br>50% particle diameter of lactose: 180 μm-250 μm<br>90% particle diameter of lactose: 270 μm-340 μm<br>(Measurement: Particle size analysis laser diffraction methods) |
| Lactose 9 | InhaLac 230 (Molkerei MEGGLE Wasserburg GmbH&Co. KG) | 10% particle diameter of lactose: 30 μm-60 μm<br>50% particle diameter of lactose: 70 μm-110 μm<br>90% particle diameter of lactose: 110 μm-150 μm<br>(Measurement: Particle size analysis laser diffraction methods) |

In addition, the air entrainment methods in Table 1 is a method for measuring particle size distribution using a sieve while stirring powder using standardized air jet. The air entrainment methods are described in the Japanese Pharmacopoeia "GENERAL TESTS, PROCESSES AND APPARATUS, 3. Powder Property Determinations, 3.04 Particle Size Determination 2.2.2 Air Entrainment Methods" (see The Japanese Pharmacopoeia Sixteenth Edition, Principles of Operation, Hirokawa-Shoten Ltd., p. 423.). After precise measurement of the mass of a sample remaining on the sieve, the test gives the weight percentage (%) of powder in each sieve size range. For example, when the diameter of a sieve is d μm, and the percentages of the weight of powder that has passed through the sieve is A wt %, the weight of the fraction with particle diameters of less than d μm is A wt %.

A preferable particle size distribution of a carrier satisfies (Condition-1), (Condition-2), (Condition-3) or (Condition-4), and more preferably satisfies (Condition-2), (Condition-3) or (Condition-4). A further preferable particle size distribution satisfies (Condition-2) or (Condition-3).

[3] Step of Mixing Particles and Carrier

The inventive particles are mixed well with a carrier to form a complex that can be stable until administration. In the specification of the present application, the complex represents a molecular aggregate formed by conjugation of the inventive particles and a carrier. Mixing of the inventive particles and a carrier can be performed by simple mixing or using a well-known mixer. The term "simple mixing" refers to mixing performed using a bottle, a polyethylene container, or a container having features similar to the container. When mixing is performed using a mixer, major examples of a mixer include a batch system and a continuous system. Examples of the batch system include two sorts, a rotated type and a stationary type. Examples of the rotated type mixer include a horizontal drum mixer, a V-shaped mixer, a double cone type mixer, a cubic type mixer, and a turbula mixer. Examples of the stationary type mixer include a screw type (vertical,horizontal) mixer, a revolution screw type mixer, and a ribbon type (vertical,horizontal) mixer. The continuous system is also divided into two sorts, a rotated type and a stationary type. As for the rotated type, a horizontal drum mixer and a level cone type mixer are known, and a screw type (vertical,horizontal) mixer, a ribbon type (vertical,horizontal) mixer, and a rotation disk type mixer are known as the stationary type. In addition, through agitation by a mixing process using an agitation granulator such as a high-speed mixer, a dry particle complexing apparatus, or the like, a uniform mixed formulation can be produced. For mixing the inventive particles and a carrier, a V-shaped mixer, a turbula mixer, an agitation granulator or a bottle, a nylon container, a polyethylene container, or containers having features similar to the same are preferable. More preferable examples thereof include a turbula mixer or a bottle, a nylon container, a polyethylene container, and containers having features similar to the same.

The weight ratio between the inventive particles and a carrier is in the range of 0.1:100 to 100:0.1. When the weight of the inventive particles is higher than this range, the particles may not be released from a capsule, a blister pack or a device. When the weight of a carrier is higher than this range, pirfenidone may lose its pharmacological activity. The weight ratio between the inventive particles and a carrier is preferably 1:100 to 10:1, more preferably 1:50 to 1:3, further preferably 1:20 to 1:5, and particularly preferably 1:5.47.

[4] Step of Mixing Carrier and Lipid

The properties of the carrier surface can also be improved by further mixing the carrier with a lipid. Specifically, with the use of the above mixer, agitation granulator, or the like, a carrier is mixed with a lipid under predetermined conditions. For mixing of a carrier with a lipid, a screw type (vertical,horizontal) mixer or an agitation granulator is preferable. A more preferable example thereof is an agitation granulator.

As a lipid to be mixed with a carrier, stearic acid, magnesium stearate, calcium stearate, sucrose fatty acid ester, sodium stearyl fumarate or lecithin is preferred. More preferably, such a lipid is stearic acid, magnesium stearate, or calcium stearate, further preferably, magnesium stearate, or calcium stearate, and particularly preferably magnesium stearate.

The proportion of a lipid to be mixed with a carrier is in the range of preferably 0.1 wt % to 10 wt % in the inventive formulation. The proportion of the same is more preferably 0.1 wt % to 5 wt %, further preferably 0.1 wt % to 2 wt %, and particularly preferably 0.5 wt % to 2 wt %.

The powder formulation of the present invention is a powder formulation for transpulmonary inhalation comprising pirfenidone, a lipid, and a carrier.

The content of pirfenidone in the inventive formulation is 0.1 wt % to 99 wt %, preferably 1 wt % to 50 wt %, more preferably 5 wt % to 30 wt %, further preferably 10 wt % to 20 wt %, and particularly preferably 15 wt %. The inventive formulation can comprise pirfenidone at a high concentration, so that the amount of the inventive formulation itself upon inhalation can be reduced.

The content of a lipid in the inventive formulation is 0.02 wt % to 5 wt %, preferably 0.02 wt % to 1 wt %, more preferably 0.02 wt % to 0.5 wt %, further preferably 0.1 wt % to 0.5 wt %, and particularly preferably 0.45 wt %. The lipid content of higher than these ranges cannot increase the concentration of the drug substance in the formulation, and poses a safety concern, and thus is not preferable. On the other hand, the lipid content of lower than these ranges may result in insufficient grinding such that a sufficient particle diameter for the inventive particles to be delivered to the lungs cannot be achieved.

The content of a carrier in the inventive formulation is 0.98 wt % to 99.88 wt %, preferably 49 wt % to 98.98 wt %, more preferably 69.5 wt % to 94.98 wt %, further preferably 79.5 wt % to 89.9 wt %, and particularly preferably 84.55 wt %. The carrier content of higher than these ranges makes it impossible to increase the concentration of the drug substance in the formulation. On the other hand, the carrier content of lower than these ranges causes the inventive particles to be unable to adhere to a carrier, and remain as fine particles, so that the formulation may remain in large amounts in capsules or devices.

In the case of the powder formulation for transpulmonary inhalation of the present invention comprising pirfenidone, a lipid and a carrier, the contents thereof are as follows. The content of pirfenidone is 0.1 wt % to 99 wt %, the lipid content is 0.02 wt % to 5 wt %, and the carrier content is 0.98 wt % to 99.88 wt %. Preferably, the content of pirfenidone is 1 wt % to 50 wt %, the lipid content is 0.02 wt % to 1 wt %, the carrier content is 49 wt % to 98.98 wt %. More preferably, the content of pirfenidone is 5 wt % to 30 wt %, the lipid content is 0.02 wt % to 0.5 wt %, and the carrier content is 69.5 wt % to 94.98 wt %. Further preferably, the content of pirfenidone is 10 wt % to 20 wt %, the lipid content is 0.1 wt % to 0.5 wt %, and the carrier content is 79.5 wt % to 89.9 wt %. Particularly preferably, the content of pirfenidone is 15 wt %, the lipid content is 0.45 wt %, and the carrier content is 84.55 wt %.

The powder formulation of the present invention is specifically a powder formulation for transpulmonary inhalation comprising pirfenidone, magnesium stearate and lactose.

The content of magnesium stearate in the inventive formulation is 0.02 wt % to 5 wt %, preferably 0.02 wt % to 1 wt %, more preferably 0.02 wt % to 0.5 wt %, further preferably 0.1 wt % to 0.5 wt %, and particularly preferably 0.45 wt %. The magnesium stearate content of higher than these ranges makes it impossible to increase the concentration of the drug substance in the formulation, and poses a safety concern, and thus is not preferable. On the other hand, the magnesium stearate content of lower than these ranges may result in insufficient grinding such that a sufficient particle diameter for the inventive particles to be delivered to the lungs cannot be achieved.

The content of lactose, particularly particulate lactose in the inventive formulation is 0.98 wt % to 99.88 wt %, preferably 49 wt % to 98.98 wt %, more preferably 69.5 wt % to 94.98 wt %, further preferably 79.5 wt % to 89.9 wt %, and particularly preferably 84.55 wt %. The particulate lactose content of higher than these ranges makes it impossible to increase the concentration of the drug substance in the formulation. On the other hand, the particulate lactose content of lower than these ranges causes the inventive particles to be unable to adhere to lactose, and remain as fine particles, and thus the formulation may remain in large amounts in capsules or devices.

In the case of the powder formulation for transpulmonary inhalation of the present invention comprising pirfenidone, magnesium stearate and lactose, and particularly particulate lactose, the contents thereof are as follows. The content of pirfenidone is 0.1 wt % to 99 wt %, the content of magnesium stearate is 0.02 wt % to 5 wt %, and the content of particulate lactose is 0.98 wt % to 99.88 wt %. Preferably, the content of pirfenidone is 1 wt % to 50 wt %, the content of magnesium stearate is 0.02 wt % to 1 wt %, and the content of particulate lactose is 49 wt % to 98.98 wt %. More preferably, the content of pirfenidone is 5 wt % to 30 wt %, the content of magnesium stearate is 0.02 wt % to 0.5 wt %, and the content of particulate lactose is 69.5 wt % to 94.98 wt %. Further preferably, the content of pirfenidone is 10 wt % to 20 wt %, the content of magnesium stearate is 0.1 wt % to 0.5 wt %, and the content of particulate lactose is 79.5 wt % to 89.9 wt %. Particularly preferably, the content of pirfenidone is 15 wt %, the content of magnesium stearate is 0.45 wt %, and the content of particulate lactose is 84.55 wt %.

[5] Capsule

A capsule may be any capsule as long as it meets the specification of the Japanese pharmacopoeial general rules for formulations. Specific examples thereof include No. 0 capsule to No. 5 capsule, and preferably No. 2 capsule. When No. 2 capsule is used, the amount of the inventive formulation is 10 mg to 80 mg, preferably 20 mg to 70 mg, more preferably 30 mg to 60 mg, and particularly preferably 40 mg. The amount of the formulation higher than these ranges causes the inventive formulation to remain in such capsules, so that the inventive formulation may not be sufficiently dispersed. The amount of the same lower than these ranges may cause insufficient exertion of medicinal effects.

[6] Inhaler

When the inventive particles obtained in the above steps are administered as the powder formulation for inhalation administration, a subject can be medicated by transpulmonary administration, and per-mucosal administration such as nasal administration, etc. When the route of administration is transpulmonary administration, specifically, capsules are set in the inhaler and can be administered using any one of inhalers to be used in the relevant field.

Examples of an inhaler that can be used herein include, but are not limited to, devices for transpulmonary administration, such as Spin haler, E-haler, Flow-Caps, Jet haler, Disk haler, Rotor haler, Inspirer ease, Inhalation eight, etc., as inhalers and quantitative atomizers, etc.

Example 1

(1) Preparation of the Inventive Particles

Table 2 shows the formulae of the inventive particles. Pirfenidone (Signa) and magnesium stearate (PETER GREVEN) were weighed and mixed within a bag. The powder mixed within the bag was subjected to jet mill grinding under the conditions shown in Table 3.

Table 2 also shows the formulae of the comparative particles. Pirfenidone was dissolved in ethanol and then lactose was dissolved in water. After these solutions were mixed, spray drying was performed using CDABT-8 closed system spray dryer (OHKAWARA KAKOHKI CO., LTD.) with RJ-10 ring jet nozzle under the conditions shown in Table 4, and thus comparative particles 1 were produced.

TABLE 2

|  | Inventive particles 1 | Inventive particles 2 | Inventive particles 3 | (wt %) Comparative particles 1 |
|---|---|---|---|---|
| Pirfenidone | 97.09 | 98.36 | 99.67 | 60.00 |
| Magnesium stearate | 2.91 | 1.64 | 0.33 | — |
| Lactose | — | — | — | 40.00 |

Note that when inventive particles 1 were produced, jet mill grinding was performed twice; and when inventive particles 2 and 3 were produced, jet mill grinding was performed 3 times.

TABLE 3

| | Conditions for use |
|---|---|
| Instrument used | Alpine spiral jet mill (HOSOKAWA MICRON) |
| Feeding method | Manual feeding |
| Supply air pressure | 0.6 MPa |
| Grinding air pressure | 0.6 MPa |
| Dust collecting method | Filter bag (PA) |

TABLE 4

| | Conditions for use |
|---|---|
| Instrument used | CDABT-8 closed system spray dryer (Ohkawara Kakohki Co., Ltd.) |
| Throughput of testing liquid (kg/h) | 1.8 |
| Inlet temperature (° C.) | 102 |
| Outlet temperature (° C.) | 67 |
| Atomizing pressure (MPa) | 0.4 |

(2) Measurement of the Particle Size Distribution of the Inventive Particles

Figure 1:
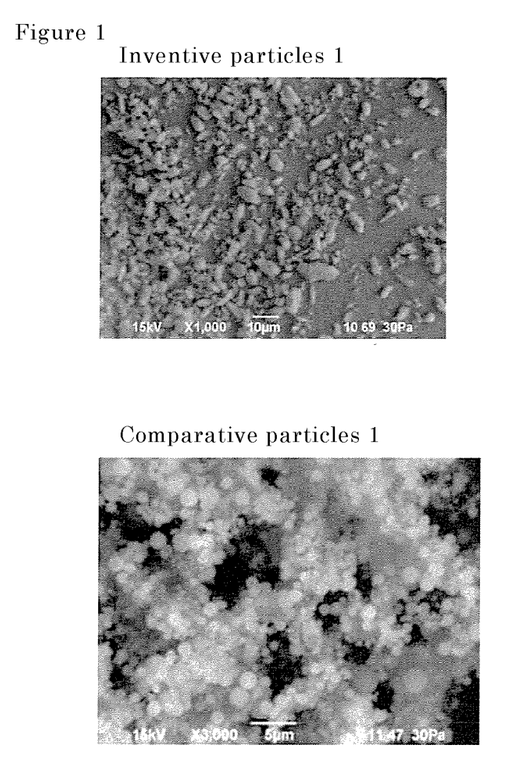
FIG. 1 shows SEM (scanning electron microscope) images of inventive particles 1 and comparative particles 1.

FIG. 1 shows the SEM (scanning electron microscope) images of inventive particles 1 and comparative particles 1. The inventive particles and the comparative particles were measured for D10, D50 and D90 using a dry laser diffraction apparatus for measuring particle size distribution (Sympatec HELOS & RODOS). Each particle diameter is shown in Table 5. Note that in Table 5, "pass" means grinding frequency.

Of the inventive particles, inventive particles 1 were found to have a mean particle diameter (D50) of about 3 μm after 2 times of jet mill grinding. Further, inventive particles 2 and 3 were found to have a mean particle diameter (D50) of 5 μm or less, and it is considered that all the inventive particles can be delivered to the bronchi and the lungs upon inhalation. On the other hand, comparative particles 1 were found to have a mean particle diameter higher than that of inventive particles 1.

TABLE 5

| | Inventive particles 1 | Inventive particles 2 | Inventive particles 3 | Comparative particles 1 |
|---|---|---|---|---|
| D10 (μm) | 1 pass 1.19 | 1 pass 1.75 | 1 pass 1.99 | 0.93 |
| | 2 pass 1.13 | 2 pass 1.29 | 2 pass 1.75 | |
| | | 3 pass 1.28 | 3 pass 1.81 | |
| D50 (μm) | 1 pass 3.21 | 1 pass 7.46 | 1 pass 5.76 | 3.73 |
| | 2 pass 3.03 | 2 pass 3.99 | 2 pass 4.26 | |
| | | 3 pass 3.35 | 3 pass 3.88 | |
| D90 (μm) | 1 pass 7.74 | 1 pass 27.36 | 1 pass 16.39 | 17.17 |
| | 2 pass 6.47 | 2 pass 10.14 | 2 pass 8.91 | |
| | | 3 pass 7.11 | 3 pass 7.36 | |

TABLE 5-continued

| | Inventive particles 1 | Inventive particles 2 | Inventive particles 3 | Comparative particles 1 |
|---|---|---|---|---|
| Proportion (%) of particles of 5 μm or less | 1 pass 74.51 2 pass 79.66 | 1 pass 35.66 2 pass 62.07 3 pass 74.57 | 1 pass 42.44 2 pass 60.66 3 pass 68.82 | 60.78 |

(3) Temporal Stability Test for the Inventive Particles

Inventive particles 1 and comparative particles 1 were subjected to a temporal stability test under humidifying and heating conditions. Conditions for the temporal stability test are as follows.

Conditions for Temporal Stability Test
  Instrument used: temperature and humidity controlled bath LH21-14M
  Conditions: 25° C. 60% RH (relative humidity), 40° C. 75% RH (relative humidity), 60° C.
  30 minutes after the start of the test (comparative particles 1 alone), the mean particle diameter was measured at 1 hour later and 3 hours later.

Figure 2:
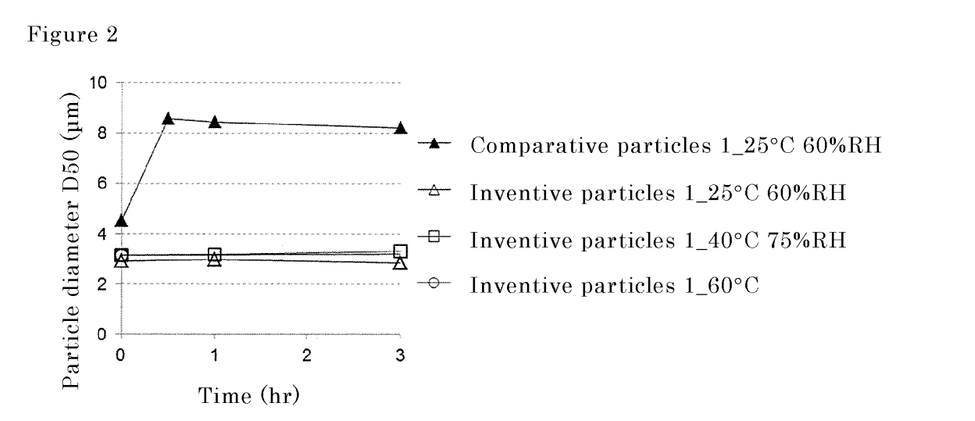
FIG. 2 shows transitions of the mean particle diameters of micronized particles under high temperatures and high humidification.

FIG. 2 shows changes in mean particle diameter over time in the temporal stability test. As a result, the mean particle diameter of inventive particles 1 remained almost unchanged at 25° C. 60% RH (relative humidity), 40° C. 75% RH (relative humidity), and 60° C. for 0 to 3 hours after the start of the test. On the other hand, the mean particle diameter of comparative particles 1 increased at 25° C. 60% RH (relative humidity) at and after 30 minutes after the start of the test. Above results revealed that inventive particles 1 produced by mixing pirfenidone and magnesium stearate and then grinding the mixture were more stable than comparative particles 1; that is, a spray-dried product.

Example 2

(1) Assessment of Inhalation Properties Based on Differences in the Concentrations of Magnesium Stearate in Formulations The inventive formulations shown in Table 6 were produced. Note that magnesium stearate was subjected in advance to jet mill grinding under the conditions of Table 3 such that the mean particle diameter was about 2 μm. Pirfenidone (Signa) and ground magnesium stearate (PETER GREVEN) were weighed and then mixed in a bag. The powder mixed in the bag was subjected to jet mill grinding under the conditions shown in Table 3. The thus ground inventive particles and lactose 3 in Table 1 (InhaLac 120 (Molkerei MEGGLE Wasserburg GmbH&Co.KG)) were mixed in a bag, thereby preparing the inventive formulations. These formulations were examined for inhalation properties using a cascade imp actor.

TABLE 6

|  | Inventive formulation 1 | Inventive formulation 2 | (wt %) Inventive formulation 3 |
|---|---|---|---|
| Pirfenidone | 15.00 | 15.00 | 15.00 |
| Magnesium stearate | 0.45 | 0.90 | 2.00 |
| Lactose | 84.55 | 84.10 | 83.00 |
| Total | 100.00 | 100.00 | 100.00 |

(2) Assessment of Formulation Using Cascade Impactor

In order to conduct investigation on the aerodynamic particle size diameter of fine powders, an examination was carried out using a cascade impactor which is an artificial respiratory tract and a lung model. The apparatus is composed of piles in eight stages and a final filter, then combined with a suction pump. The fundamental method, which is a procedure described in "AERODYNAMIC SIZE DISTRIBUTION" of USP 34 "Physical Tests and Determinations" was applied. The specified method is as follows.
(Method)
Apparatus: Andersen cascade impactor (COPLEY)
Pump flow rate: 28.3 L/min
Time: 8.5 seconds
A Japanese Pharmacopoeia No. 2 capsule was filled with 40 mg of each sample, and was placed in the device.
Method of assay: Ultraviolet spectrophotometer (8453, Agilent)
Cell length: 10 mm
Wavelength: 222 nm
Test liquid: water/methanol (50:50)

FPF (fine particle fraction) is the ratio of the amount of particles delivered to stages 2 to 7 (in vitro amount delivered) of a cascade impactor to the total amount discharged from a device (inhaler). Specifically, FPF is the ratio of the amount of powder delivered to the lungs to the amount of powder actually dispersed in expiration (amount discharged outside the device). This is represented by the following equation.

FPF (%)=(amount delivered to stages 2 to 7 (in vitro amount delivered)/total amount discharged from the device)×100

In the equation, the term "total amount discharged from the device" refers to a value produced by subtracting the amount of particles adhered to the capsule and the device from the total amount of particles with which the capsule is filled (amount of pirfenidone: 6 mg).

Delivery dose (%) at stages 2 to 7 is represented by the following equation.

Delivery dose (%) at stages 2 to 7=(amount delivered to stages 2 to 7 (in vitro amount delivered)/amount of particles with which a capsule is filled (amount of pirfenidone: 6 mg))×100

Figure 3:
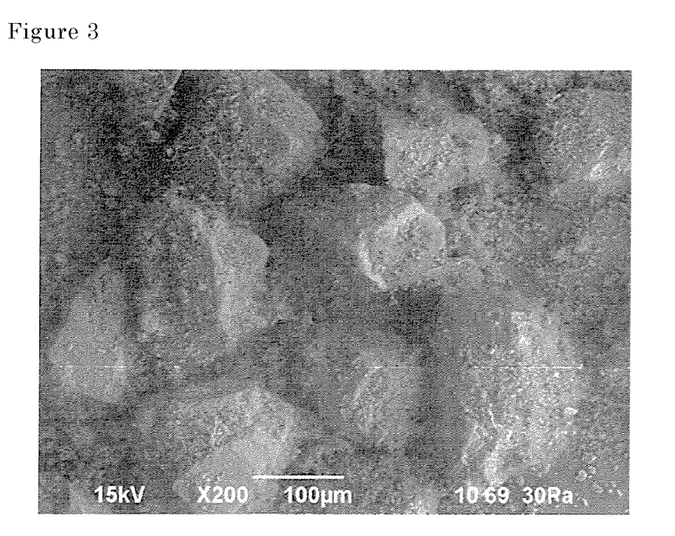
FIG. 3 shows an SEM (scanning electron microscope) image of inventive formulation 1.
Figure 4:
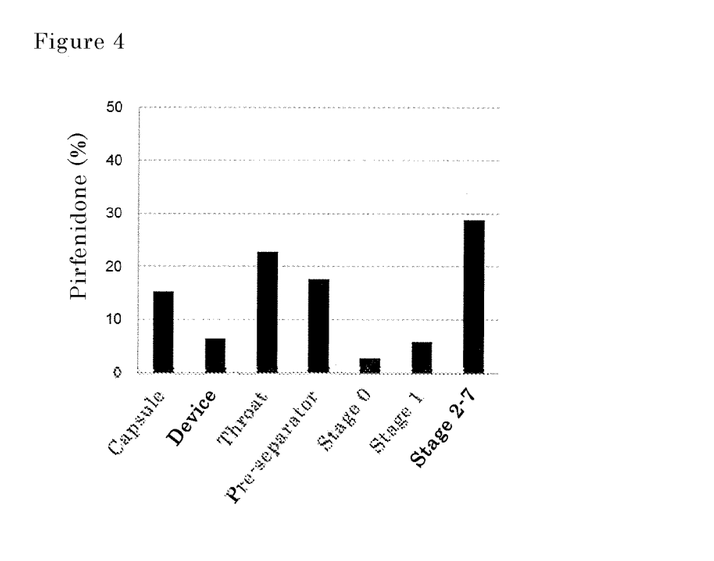
FIG. 4 shows the amounts of pirfenidone in a capsule, a device and on each stage of a cascade impactor body.

(Result) FIG. 3 shows a SEM (scanning electron microscope) image of inventive formulation 1. Furthermore, FIG. 4 shows the amounts of pirfenidone of inventive formulation 1 in the capsule, the device, and on each stage of the cascade impactor body. The proportion of the sum of the amounts of pirfenidone distributed on stages 2 to 7 relative to the total amount of pirfenidone distributed in the throat, on the pre-separator and on stages 0 to 7 is defined as FPF (%), "the percentage of fine particles reaching target sites, the bronchi or the lungs". Table 7 shows FPF values of inventive formulations 1 to 3 and the delivery dose (%) at stages 2 to 7. As a result, inventive formulation 1 containing magnesium stearate in an amount of 0.45 wt % exhibited high FPF value and high delivery dose (%) at stages 2 to 7, so that it is concluded that pirfenidone can be delivered to lungs.

TABLE 7

|  | Inventive formulation 1 | Inventive formulation 2 | Inventive formulation 3 |
| --- | --- | --- | --- |
| FPF (%) | 37.0 | 33.6 | 20.1 |
| Delivery dose at stages 2 to 7 (%) | 28.9 | 26.7 | 16.1 |

Example 3

(1) Assessment of Inhalation Properties Based on Differences in Pirfenidone Concentrations in Formulations The inventive formulations as shown in Table 8 and Table 9 were produced. Note that magnesium stearate was subjected in advance to jet mill grinding under the conditions of Table 3 such that the mean particle diameter was about 2 µm. Pirfenidone (Signa), and ground magnesium stearate (PETER GREVEN) were weighed and then mixed in a bag. The powder mixed in the bag was subjected to jet mill grinding under the conditions shown in Table 3. The ground inventive particles and lactose 3 (InhaLac 120 (Molkerei MEGGLE Wasserburg GmbH&Co.KG)) in Table 1 were mixed in a bag, thereby producing the inventive formulations. These formulations were examined for inhalation properties using a cascade impactor.

TABLE 8

|  | | (wt %) |
| --- | --- | --- |
|  | Inventive formulation 1 | Inventive formulation 4 |
| Pirfenidone | 15.00 | 7.50 |
| Magnesium stearate | 0.45 | 0.45 |
| Lactose | 84.55 | 92.05 |
| Total | 100.00 | 100.00 |

TABLE 9

|  | | | (wt %) |
| --- | --- | --- | --- |
|  | Inventive formulation 5 | Inventive formulation 6 | Inventive formulation 7 |
| Pirfenidone | 15.00 | 12.50 | 7.50 |
| Magnesium stearate | 2.00 | 2.00 | 2.00 |
| Lactose | 83.00 | 85.50 | 90.50 |
| Total | 100.00 | 100.00 | 100.00 |

(Result) The FPF values and delivery dose (%) at stages 2 to 7 of inventive formulations 1, 4, and 5 to 7 are shown in Table 10 and Table 11. As a result, in Table 10, when the magnesium stearate concentration was 0.45 wt % and the pirfenidone concentration was varied, even inventive formulation 1 having a pirfenidone concentration as high as 15 wt % exhibited a high FPF value and high delivery dose at stages 2 to 7. When the magnesium stearate concentration was 2.0 wt % and the pirfenidone concentration was varied, inventive formulation 6 having a pirfenidone concentration of 12.5 wt % exhibited a high FPF value and high delivery dose at stages 2 to 7. Accordingly, it is considered that the inventive formulations even having a high pirfenidone concentration in the formulations enable to deliver pirfenidone to lungs.

TABLE 10

|  | Inventive formulation 1 | Inventive formulation 4 |
| --- | --- | --- |
| FPF (%) | 37.0 | 31.6 |
| Delivery dose at stages 2 to 7 (%) | 28.9 | 24.5 |

TABLE 11

| | Inventive formulation 5 | Inventive formulation 6 | Inventive formulation 7 |
|---|---|---|---|
| FPF (%) | 20.1 | 36.9 | 25.7 |
| Delivery dose at stages 2 to 7 (%) | 16.1 | 28.6 | 20.6 |

Example 4

(1) Assessment of Inhalation Properties Based on Grade Differences of Magnesium Stearate The inventive formulations shown in Table 12 were produced. Magnesium stearate was subjected to jet mill grinding under the conditions of Table 3 such that the mean particle diameter was about 2 μm. Pirfenidone (Signa) and ground magnesium stearate (light) (Taihei Chemical Industrial Co., Ltd.) or ground magnesium stearate (for inhalation) (PETER GREVEN) were weighed and then mixed in a bag. The powder mixed in the bag was subjected to jet mill grinding under the conditions shown in Table 3. The ground inventive particles and lactose 3 in Table 1 (InhaLac 120 (Molkerei MEGGLE Wasserburg GmbH&Co.KG) were mixed in a bag, thereby producing the inventive formulations. These formulations were examined for inhalation properties using a cascade impactor.

TABLE 12

| | | (wt %) |
|---|---|---|
| | Inventive formulation 1 | Inventive formulation 8 |
| Pirfenidone | 15.00 | 15.00 |
| Magnesium stearate | 0.45 (light) | 0.45 (for inhalation) |
| Lactose | 84.55 | 84.55 |
| Total | 100.00 | 100.00 |

(Result) Table 13 shows the FPF values and delivery dose at stages 2 to 7 of inventive formulations 1 and 8. As a result, both the formulation containing pirfenidone at a concentration of 15 wt % and magnesium stearate (light) and the formulation containing pirfenidone at the same concentration and magnesium stearate (for inhalation) exhibited almost the same FPF values and delivery dose at stages 2 to 7.

TABLE 13

| | Inventive formulation 1 | Inventive formulation 8 |
|---|---|---|
| FPF (%) | 37.0 | 39.8 |
| Delivery dose at stages 2 to 7 (%) | 28.9 | 28.7 |

Example 5

(1) Assessment of the Mean Particle Diameters of the Inventive Particles Based on Differences in the Concentration of Magnesium Stearate in Formulations The inventive particles shown in Table 14 were produced. Note that magnesium stearate was subjected to jet mill grinding in advance under the conditions of Table 3 such that the mean particle diameter was about 2 μm. Pirfenidone (Signa) and ground magnesium stearate (PETER GREVEN) were weighed and then mixed in a bag. The powder mixed in the bag was subjected to jet mill grinding under the conditions of Table 3. Note that when the inventive particles were produced, jet mill grinding was performed 3 times. The mean particle diameter (D50) of the ground inventive particles was measured using a dry laser diffraction apparatus for measuring particle size distribution (Sympatec HELOS & RODOS). Each particle diameter is shown in Table 15.

TABLE 14

| | | | | | | (wt %) |
|---|---|---|---|---|---|---|
| | Inventive particles 1 | Inventive particles 2 | Inventive particles 3 | Inventive particles 4 | Inventive particles 5 | Inventive particles 6 |
| Pirfenidone | 15 | 15 | 15 | 15 | 15 | 15 |
| Magnesium stearate | 3 | 1.5 | 0.45 | 0.03 | 0.015 | 0 |

TABLE 15

| | Grinding frequency | | |
|---|---|---|---|
| | 1 pass | 2 pass | 3 pass |
| Inventive particles 1 | 2.44 μm | 2.10 μm | 2.01 μm |
| Inventive particles 2 | 3.15 μm | 2.47 μm | 2.07 μm |
| Inventive particles 3 | 3.78 μm | 3.14 μm | 3.04 μm |
| Inventive particles 4 | 5.29 μm | 4.92 μm | 4.82 μm |
| Inventive particles 5 | 6.82 μm | 5.25 μm | 5.12 μm |
| Inventive particles 6 | 6.47 μm | 6.30 μm | 6.01 μm |

(Result)

When the magnesium stearate concentration was 0 and the same was 0.015 wt %, a mean particle diameter of 5 μm or less could not be achieved. On the other hand, when the magnesium stearate concentration was 0.03 wt %, a mean particle diameter of 5 μm or less could be achieved. Furthermore, the higher the concentration of magnesium stearate in the formulation, the more decreased mean particle diameter of the inventive particles.

However, if the amount of magnesium stearate is high, the concentration of the drug substance in the formulation cannot be increased and there is a safety concern.

Therefore, the content of magnesium stearate in the formulation is preferably 0.02 wt % to 5 wt %.

INDUSTRIAL APPLICABILITY

The present invention is useful as a pharmaceutical composition for treatment of lung diseases.

The invention claimed is:

1. A powder formulation comprising a micronized particle and a carrier,
   wherein the micronized particle comprises pirfenidone and magnesium stearate and has a mean particle diameter of 5 µm or less,
   wherein a content of the magnesium stearate is 0.02 wt % to 0.90 wt % of the powder formulation, and
   wherein a content of the pirfenidone is 12.5 wt % to 15.0 wt % of the powder formulation.

2. The powder formulation according to claim 1, wherein a weight ratio between the pirfenidone and the magnesium stearate is in the range of 10:1 to 500:1.

3. The powder formulation according to claim 1, wherein the carrier is selected from the group consisting of a saccharide, a sugar alcohol and a macromolecular polymer.

4. The powder formulation according to claim 1, wherein the carrier is a saccharide, and the saccharide is selected from the group consisting of lactose, glucose, saccharose, trehalose and sucrose.

5. The powder formulation according to claim 4, wherein the carrier is a saccharide, and the saccharide is lactose.

6. The powder formulation according to claim 1, wherein the carrier is a sugar alcohol, and the sugar alcohol is selected from the group consisting of erythritol, mannitol and sorbitol.

7. The powder formulation according to claim 1, wherein the carrier is a macromolecular polymer, and the macromolecular polymer is selected from the group consisting of calcium carmellose, polyvinyl pyrrolidone and methylcellulose.

8. The powder formulation according to claim 1, wherein the carrier has a mean particle diameter of 10 µm to 250 µm.

9. The powder formulation according to claim 1, wherein a weight ratio between the micronized particle and the carrier is 0.1:100 to 100:0.1.

10. The powder formulation according to claim 1, wherein the content of the magnesium stearate is 0.02 wt % to 0.5 wt % of the powder formulation.

11. The powder formulation according to claim 1, wherein the content of the magnesium stearate is 0.02 wt % to 0.5 wt % of the powder formulation, the carrier is lactose, and the content of the lactose is 69.5 wt % to 94.98 wt % of the powder formulation.

12. A process for producing the powder formulation according to claim 1, comprising mixing pirfenidone and magnesium stearate, wherein a content of the magnesium stearate is 0.02 wt % to 0.90 wt % of the powder formulation and a content of the pirfenidone is 12.5 wt % to 15.0 wt % of the powder formulation, then micronizing the mixture by grinding the mixture using a jet mill grinder to produce a micronized particle, and then combining the micronized particle with a carrier to obtain the powder formulation.

13. A process for producing the powder formulation according to claim 1, comprising grinding pirfenidone in the coexistence of magnesium stearate to obtain a micronized particle comprising pirfenidone and magnesium stearate and having a mean particle diameter of 5 µm or less, wherein a content of the magnesium stearate is 0.02 wt % to 0.90 wt % of the powder formulation and a content of the pirfenidone is 12.5 wt % to 15.0 wt % of the powder formulation, and mixing the micronized particle with a carrier to obtain the powder formulation.

* * * * *